(12) United States Patent
Trumpp et al.

(10) Patent No.: US 8,329,160 B2
(45) Date of Patent: Dec. 11, 2012

(54) INTERFERON ALPHA SEQUENTIAL REGIMEN FOR TREATING CANCERS

(75) Inventors: Andreas Trumpp, Heidelberg (DE); Marieke Essers, Pully (CH)

(73) Assignee: HI-Stem (DE)

( * ) Notice: Subject to any disclaimer, the term of this patent is extended or adjusted under 35 U.S.C. 154(b) by 0 days.

(21) Appl. No.: 12/664,726

(22) PCT Filed: Jun. 13, 2008

(86) PCT No.: PCT/IB2008/052343
§ 371 (c)(1),
(2), (4) Date: Mar. 9, 2010

(87) PCT Pub. No.: WO2008/152609
PCT Pub. Date: Dec. 18, 2008

(65) Prior Publication Data
US 2010/0196320 A1    Aug. 5, 2010

Related U.S. Application Data

(60) Provisional application No. 60/929,175, filed on Jun. 15, 2007.

(51) Int. Cl.
*A61K 38/21* (2006.01)
*C07K 14/56* (2006.01)
(52) U.S. Cl. ...................................... 424/85.7; 530/351
(58) Field of Classification Search .................. None
See application file for complete search history.

(56) References Cited

U.S. PATENT DOCUMENTS

2001/0021783 A1* 9/2001 Bouchard et al. ............. 549/510

FOREIGN PATENT DOCUMENTS

EP         0 433 765 A1    6/1991

OTHER PUBLICATIONS

Kantarjian H, et al. Analysis of the impact of Imatinib mesylate therapy on the prognosis of patients with Philadelphia chromosome-positive chronic myelogenous leukemia treated with interferon-alpha regimens for early chronic phase. Cancer, 2003, vol. 98, p. 1430-1437.*
Trumpp A, et al. Awakening dormant haematopoietic stem cells. Nature Reviews Immunology, 2010, vol. 10, p. 201-209.*
Essers M.A.G, et al. IFNa activates dormant haematopoietic stem cells in vivo. Nature, 2009, vol. 458, p. 904-909.*
Grandér, et al., "Interferon and Malignant Disease-How Does it Work and Why Doesn't It Always?," Acta Oncologica, vol. 37, No. 4, pp. 331-338 (1998).
Reya et al., "Stem cells, cancer, and cancer stem cells," Nature, vol. 414, pp. 105-111 (Nov. 2001).
Polyak et al., "Roots and stems: stem cells in cancer," Nature Medicine, vol. 11, 12, pp. 296-300 (2006).
Le Bon et al., Cross-priming of CD8+ T cells stimulated by virus-induced type I interferon, Nature Immunology, vol. 4, No. 10, pp. 1009-1015 (Oct. 2003).
Wilson et al., "c-Myc controls the balance between hematopoietic stem cell self-renewal and differentiation," Genes & Development, No. 18, pp. 2747-2763 (2004).
Falkson, et al., "Improved Results With the Addition of Interferon alfa-2b to Dacarbazine in the Treatment of Patients With Metastatic Malignant Melanoma," Journal of Clinical Oncology, vol. 9, No. 8, pp. 1403-1408 (Aug. 1991).
Legha, "The Role of Interferon Alfa in the Treatment of Metastatic Melanoma," Seminars in Oncology, vol. 24, No. 1, Suppl. 4, pp. S4-24-S4-31 (1997).
La Rosée, et al., "Insights from pre-clinical studies for new combination treatment regimens with the Bcr-Abl kinase inhibitor imatinib mesylate (Gleevec/Glivec) in chronic myelogenous leukemia: a translational perspective," Leukemia, vol. 16, pp. 1213-1219 (2002).
Chabot, et al., "Alteration of dacarbazine pharmacokinetics after interleukin-2 administration in melanoma patients," Cancer Chemotherapy Pharmacology, vol. 27, No. 2, pp. 157-160 (1990).
International Search Report mailed Nov. 11, 2008 in corresponding International Application No. PCT/IB2008/052343 (English language).
Litvinova E, "Study of Tumor Cells Sensitivity in Patients With Acute Leukemia to Cytokines and Their Combined Use With Drugs in Vitro by MTT Analysis," Vestnik Rossi Akademii Meditsinskikh Nauk, vol. 6, pp. 16-21 (2000). (English language interpretation).
Alexander Roesch, et al., "A Temporarily Distinct Supopulation of Slow-Cycling Melanoma Cells Is Required for Continuous Tumor Growth," Cell, 141, pp. 583-594, May 14, 2010.
Ossowski, et al., "Dormancy of Metastatic Melanoma," NIH Public Access, Author Manuscript, Published in final edited form as: Pigment Cell Melanoma Res., 23(1):41.doi:10.1111/j.1755-148X.2009.00647.x., pp. 1-24, Feb. 2010.
Notice of Reasons for Rejection dated Jul. 10, 2012 in corresponding Japanese Patent Application No. 2010-511773 (with English translation).
J. Atzpodien, et al., "Biochemotherapy of Advanced Metastatic Renal-Cell Carcinoma: Results of the Combination of Interleukin-2, Alpha-Interferon, 5-Fluorouracil, Vinblastine, and 13-Cis-Retinoic Acid," World Journal of Urology, 1995, vol. 13, No. 3, pp. 174-177.

* cited by examiner

*Primary Examiner* — Robert Landsman
*Assistant Examiner* — Bruce D Hissong
(74) *Attorney, Agent, or Firm* — Ostrolenk Faber LLP (57) ABSTRACT

The present invention relates to a method of treating cancers, especially those showing resistance to classical anti-pro liferative chemotherapy drugs. Further, the invention provides a specific interferon alpha sequential regimen for treating cancers, especially those showing resistance to classical anti-proliferative chemotherapy drugs such as stem cell driven cancers. More specifically, the invention relates to a use of IFN alpha for the preparation of a pharmaceutical formulation for the treatment of cancers wherein the pharmaceutical formulation is to be administered following a sequential administration pattern i.e. an induction period wherein a therapeutically effective amount of IFN alpha is administered, a period during which no IFN alpha is administrated and a chemotherapy period wherein a therapeutically effective amount of a chemotherapeutic agent is administered.

17 Claims, 10 Drawing Sheets

|       | pI:C injections | 5-FU injections | monitor survival |
|-------|-----------------|-----------------|------------------|
| day   | -9 -8 -7 -6 -5 -4 -3 -2 -1 | 0          7    |                  |
| c     |                 | 5-FU       5-FU |                  |
| day 1 |             pI:C    pI:C | 5-FU       5-FU |                  |
| day 2 |         pI:C    pI:C     | 5-FU       5-FU |                  |
| day 3 |     pI:C    pI:C         | 5-FU       5-FU |                  |
| day 5 |   pI:C  pI:C             | 5-FU       5-FU |                  |
| day 7 | pI:C  pI:C               | 5-FU       5-FU |                  |

INTERFERON ALPHA SEQUENTIAL REGIMEN FOR TREATING CANCERS

CROSS REFERENCE TO RELATED APPLICATIONS

The present application is a 35 U.S.C. §371 National Phase conversion of PCT/IB2008/052343, filed Jun. 13, 2008, which claims benefit of U.S. Provisional Application No. 60/929,175, filed Jun. 15, 2007, the disclosure of which is incorporated herein by reference. The PCT International Application was published in the English language.

FIELD OF THE INVENTION

The present invention relates to a method of treating cancers, especially those showing resistance to classical anti-proliferative chemotherapy drugs. Further, the invention provides a specific interferon alpha sequential regimen for treating cancers, especially those showing resistance to classical anti-proliferative chemotherapy drugs such as stem cell driven cancers. More specifically, the invention relates to a use of IFN alpha for the preparation of a pharmaceutical formulation for the treatment of cancers wherein the pharmaceutical formulation is to be administered following a sequential administration pattern.

BACKGROUND OF THE INVENTION

Type I interferons (IFNα/β) constitute a family of secreted proteins with pleiotropic cellular effects including inhibition of cell proliferation, induction of differentiation, modulation of the immune system and alterations of the cell surface. These activities have promoted their use in the clinic mainly in malignant and viral diseases. Interferon alpha (IFNα) has been used in the clinic for haematological malignancies, solid tumours and viral syndromes. Unfortunately, their use as anti-cancer drugs have shown only limited success, and in situations where they display clinical benefit their mechanism of action remains unclear (*Grander and Einhorn*, 1998, *Acta Oncol.*, 37, 331-338). Overall, IFNα has only limited activity on neoplams and severe cancers are resistant to the anti-proliferative action induced by Type I interferons.

Recent experimental models (*Reya et al.*, 2001, *Nature*, 414, 105-111; *Polyak and Hahn*, 2006, *Nature Med.*; 11: 296-300) support the hypothesis that many cancers are driven by a small number of so called "cancer stem cells" (CSCs). These CSCs are presumed to be resistant to classical anti-proliferative chemotherapy drugs. Despite the fact that the tumour mass is reduced by the chemotherapy that eliminates dividing cells, the frequently observed re-occurrence of the disease is caused by new tumour cells generated by chemotherapy-resistant, and thus surviving CSCs. One of the reasons CSCs are thought to be resistant to chemotherapy is their general quiescence, which is also known as dormancy Therefore, there is a clear need in the art for novel approaches towards treating and managing cancers, especially those showing resistance to classical anti-proliferative chemotherapy drugs such as stem cell driven cancers (*Polyak and Hahn*, 2006, above).

SUMMARY OF THE INVENTION

The present invention is directed towards a method of treating cancers, especially those showing resistance to classical anti-proliferative chemotherapy drugs such as stem cell driven cancers. Further, the invention provides a specific Interferon alpha regimen for treating cancers, especially those showing resistance to classical anti-proliferative chemotherapy drugs such as stem cell driven cancers. Such method and use are useful in treating cancers, especially those showing resistance to classical anti-proliferative chemotherapy drugs such as stem cell driven cancers. For example, the methods and use according to the invention are useful in the treatment of cancer stem cell driven malignancies such as leukemias, lymphomas and melanoma. The methods and use according to the invention are such that the said treatment comprises a sequential administration pattern comprising an induction treatment followed by a chemotherapy treatment.

Figure 4:
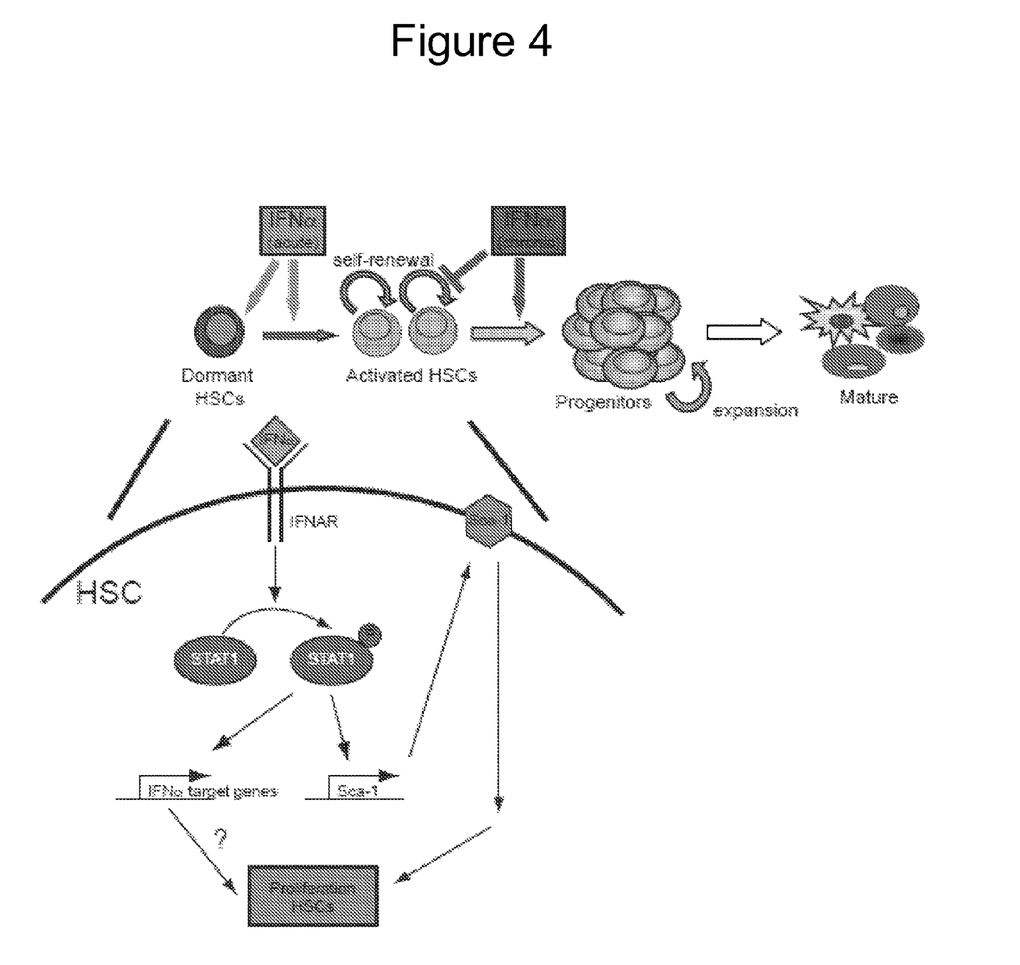
FIG. 4: Top: Model showing the activating effect of short-term (acute) IFNα stimulation on dormant/quiescent HSCs and the inhibitory effect of chronic IFNα treatment on HSC self-renewal. Bottom: IFNα binds to and activates the IFNAR resulting in the phosporylation of STAT1 leading to the expression of a number of IFNα target genes. One of these, Sca-1, is up-regulated on the mRNA level and the Sca-1 protein is incorporated into the plasma membrane. Although the signalling pathway downstream of Sca-1 remains unknown, it is required for IFNα induced proliferation since Sca-1$^{-/-}$ mice do not respond to IFNα stimulation.

It has been found that IFNα has a strong, unanticipated effect on hematopoietic stem cells (HSCs) by inducing efficient activation and cell cycle entry of quiescent HSCs (KLS CD150+CD34− CD48−), making them sensitive to classical anti-proliferative chemotherapeutics and thus allowing their specific elimination. Dormant HSCs are activated to proliferate and self-renew *in vivo*. Pulsed IFNα treatment also increases the total number of HSCs in the organism. Strikingly, this activation effect on HSCs is directly opposite to its growth inhibitory effect described in all other cell types (summarized in FIG. 4).

A first aspect of the invention provides a use of IFN alpha for the preparation of a pharmaceutical formulation for the treatment of a cancer wherein the pharmaceutical formulation is to be administered following an administration pattern comprising the sequential steps below:
(i) An induction period wherein a therapeutically effective amount of IFN alpha is administered; then
(ii) An IFN alpha-free period wherein no IFN alpha is administered; and then
(iii) A chemotherapy period wherein a therapeutically effective amount of a chemotherapeutic agent is administered.

A second aspect of the invention relates to a method for the treatment of a cancer, comprising the administration of IFN alpha or of a pharmaceutical formulation thereof in a patient in need thereof comprising the following steps:
(i) An induction period wherein a therapeutically effective amount of IFN alpha is administered; then
(ii) An IFN alpha-free period wherein no IFN alpha is administered; and then
(iii) A chemotherapy period wherein a therapeutically effective amount of a chemotherapeutic agent is administered.

Other features and advantages of the invention will be apparent from the following detailed description.

DESCRIPTION OF THE FIGURES

FIG. 1.

FIG. 1D shows the activating effect of polyIC (pI:c) treatment on dormant HSCs. After a period of permanent BrdU labeling for 10 days, mice were kept without BrdU for 70 days. 14 days before the analysis, the mice were either treated three times with polyIC or with PBS. 10 days later (and 70 days after the last BrdU injection) three HSC populations containing an increasing percentage of dormant HSCs were isolated and analysed for the presence of BrdU+label-retaining cells (LRCs), which represent dormant HSCs. In mice treated with polyIC, the percentage of BrdU+-LRCs is strongly reduced as HSCs have been activated to proliferate and have therefore lost the BrdU label.

FIG. 2.

FIG. 3: FIG. 3 represents the survival rate of mice receiving a repeated treatment with the chemotherapeutic agent 5FU, which causes a massive myeloid ablation due to elimination of all proliferating cells as described in Example 4.

DETAILED DESCRIPTION OF THE INVENTION

The term "cancer" is used herein refers to cancers such as leukemias, lymphomas and melanoma as well as all other cancers driven by cancer stem cells. Further, the term "cancer" encompasses cancers which as resistant to classical anti-proliferative chemotherapy and cancer stem cell (also called quiescent cancer cells or dormant cancer cells) driven malignancies.

As used herein, "treatment" and "treating" and the like generally mean obtaining a desired pharmacological and physiological effect. The effect may be therapeutic in terms of a partial or complete cure of a disease, condition, symptom or adverse effect attributed to the disease and/or may be prophylactic in terms of preventing or partially preventing the re-occurrence of a disease (relapse), symptom or condition thereof. The term "treatment" as used herein covers any treatment of a disease in a mammal, particularly a human, and includes: (a) inhibiting the disease, i.e. arresting or slowing its development; or relieving the disease, i.e. causing regression of the disease and/or its symptoms or conditions; (b) preventing the disease from re-occurring in a subject which may be predisposed to the re-occurrence of the disease (relapse). In particular a treatment according to the invention encompasses preventing, treating or ameliorating disease state of cancers, especially cancers which as resistant to classical anti-proliferative chemotherapy and cancer stem cell driven malignancies.

An "Induction treatment" or "priming" consists in the sequential succession of (i) an induction period wherein IFN alpha or an IFN alpha pharmaceutical composition is administered and (ii) an IFN alpha-free period. Typically, an induction period lasts up to about 1, 2, 3 or about 4 days. For example, an induction period lasts from about 1 to about 2 days. During an induction period, the IFN alpha or an IFN alpha pharmaceutical composition can be administered once or several times. Typically, during an induction period, the IFN alpha or an IFN alpha pharmaceutical composition is administered once or two times.

An "IFN alpha-free period" is a period wherein no IFN alpha is administered to the patient.

During an IFN alpha-free period, the patient can be free of any chemotherapy administration or be dosed with a placebo-pill. Typically, an IFN alpha-free period lasts up to about 2, 3, 4 or about 5 days. For example, an IFN alpha-free period lasts from about 2, 3 or about 4 days such as between about 2 to 3 days.

A "Chemotherapy treatment" consists in a chemotherapy period wherein a chemotherapeutic agent or a pharmaceutical composition thereof is administered.

Typically, a chemotherapy period lasts for up to about 1 or 2 months. For Example, a chemotherapy period lasts for up to about 1 month. In another embodiment, a chemotherapy period lasts for up to about 1 or two weeks. The chemotherapeutic period may be adapted from one chemotherapeutic agent to another one. A "Chemotherapy free period" consists in a period wherein no IFN alpha and no chemotherapeutic agent is administered to the patient. Typically, a chemotherapy free period lasts for up to about 1 or 2 months.

The term "subject" as used herein refers to mammals. For examples, mammals contemplated by the present invention include human, primates, domesticated animals such as cattle, sheep, pigs, horses and the like.

"Relapses" involve the re-occurrence of the disease after a chemotherapy treatment. The relapses are thought to be caused by new tumor cells generated by anti-proliferative chemotherapy-resistant, and thus surviving cancer stem cells (CSCs), which is thought to be due to their "quiescence", also known as "dormancy".

"Efficacy" of a treatment according to the invention can be measured based on changes in the course of disease in response to a use according to the invention. For example, treatment of cancer efficacy can be measured by decrease of cancer cells/cancer stem cells. The term "derivative" is used herein, refers to any compound having substantial structure-activity relationships to a parent compound such that the derivative has similar biochemical activity as the parent compound.

"A week" refers to a period of time of or about 5, about 6 or about 7 days.

"A month" refers to a period of time of or about 28, about 29, about 30 or about 31 days.

Interferon Alpha

The term "Interferon-alpha (IFN-alpha or IFN α)", as used herein, is intended to include Interferon α 2a, such as recombinant Interferon α −2a, e.g. recombinant human Interferon α −2a produced in *Escherichia coli* bacterium (ROFERON®, Roche). IFN-alpha further encompasses IFN-alpha derivatives such as IFN-alpha conjugates such as pegylated Interferon α 2a (PEGASYS®, Roche). Typically IFNα is at $10 \times 10^3$ units/g.

Chemotherapeutic Agents

The term "chemotherapeutic agent", as used herein, is intended to include anti-neoplastic or antimetabolite agents such as for example those used in the treatment of leukemias, lymphomas and melanoma. For example, the term chemotherapeutic agent includes pyrimidinone-based anti-neoplastic agents such as Cytarabine (Cytosar®, Pfizer) or 5-flurouracil or Cisplatin, or taxens or derivatives thereof. The term chemotherapeutic agent also includes BCR-ABL kinase inhibitors for example those used in the treatment of leukemias such as Imatinib (Gleevec®). The BCR-ABL kinase inhibitors may be used in combination with other anti-neoplastic or antimetabolite agents.

Compositions

The invention provides methods and use for the preparation of a pharmaceutical formulation for treating a patient, preferably a mammalian patient, and most preferably a human patient who is suffering from a cancer, and in particular a cancer resistant to classical anti-proliferative chemotherapy and cancer stem cell driven malignancies.

IFN alpha may be administered as a pharmaceutical formulation which can contain one or more IFN alpha in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The chemotherapeutic agent may be administered as a pharmaceutical formulation which can contain one or more chemotherapeutic agent in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The IFN alpha and/or the chemotherapeutic agent of the invention, together with a conventionally employed adjuvant, carrier, diluent or excipient may be placed separately into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. IFN alpha compositions according to the invention are preferably injectable.

Compositions of this invention may also be liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences,* 20*th* Edition, 2000, Marck Publishing Company, Easton, Pa., which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone.

Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides.

Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the *stratum corneum*, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of Administration

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Compositions of this invention may be administered in any manner including, but not limited to, orally, parenterally, sublingually, transdermally, rectally, transmucosally, via inhalation, via buccal or intranasal administration, or combinations thereof. Parenteral administration includes, but is not limited to, intravenous, intra-arterial, intra-peritoneal, subcutaneous, intramuscular, intra-thecal and intra-articular. The compositions of this invention may also be administered in the form of an implant, which allows slow release of the compositions as well as a slow controlled i.v. infusion. In a preferred embodiment, IFNα or a pharmaceutical formulation thereof is administered intravenously or subcutaneously. A dosage regimen for IFNα and the chemotherapeutic agent may be adjusted to provide the optimum therapeutic response. For example, several divided doses may be administered daily, a single dose may be administered daily, or the dose may be proportionally reduced as indicated by the exigencies of the therapeutic situation.

This invention is further illustrated by the following examples that are not intended to limit the scope of the invention in any way.

Combination

According to the invention, the chemotherapeutic agent can be administered alone or in combination with at least one additional chemotherapeutic agent, prophylactically or therapeutically to an individual prior to, simultaneously or sequentially with other therapeutic regimens or agents (e.g. multiple drug regimens), in a therapeutically effective amount, especially therapeutic agents for the treatment of cancers. Chemotherapeutic agents that are administered simultaneously with other chemotherapeutic agents can be administered in the same or different compositions and in the same or different routes of administration. However, in the context of the invention the administration of the chemotherapeutic agent is always performed sequentially after the IFNα administration, according to the regimen of the invention.

Patients

In an embodiment, patients according to the invention are patients suffering from a cancer, such as a cancer resistant to classical anti-proliferative chemotherapy and cancer stem cell-driven malignancies.

In a further embodiment, patients according to the invention are patients suffering a disease selected from leukemias, lymphomas and melanoma.

Use According to the Invention

Within the context of this invention, the beneficial effect of compositions and use according to the invention includes but is not limited to an attenuation, reduction, decrease or diminishing of the pathological development after onset of the disease. In a particular embodiment, the use and the method according to the invention have a beneficial effect on the re-occurrence of the disease (relapse) by decreasing the relapsing events and/or by potentiating the efficacy of the chemotherapeutic agents.

In one embodiment, the invention provides a use of IFN alpha for the preparation of a pharmaceutical formulation for the treatment of a cancer wherein the pharmaceutical formulation is to be administered following an administration pattern comprising the sequential steps below:

(i) An induction period wherein a therapeutically effective amount of IFN alpha is administered; then
(ii) An IFN alpha-free period wherein no IFN alpha is administered; and then
(iii) A chemotherapy period wherein a therapeutically effective amount of a chemotherapeutic agent is administered.

In another embodiment, the invention provides a method for the treatment of a cancer, comprising the administration of IFN alpha or of a pharmaceutical formulation thereof in a patient in need thereof comprising the following steps:

(i) An induction period wherein a therapeutically effective amount of IFN alpha is administered; then
(ii) An IFN alpha-free period wherein no IFN alpha is administered; and then
(iii) A chemotherapy period wherein a therapeutically effective amount of a chemotherapeutic agent is administered.

In a further embodiment, the invention provides a use or a method according to the invention wherein the induction period lasts up to about 2, 3 or about 4 days.

In another further embodiment, the invention provides a use or a method according to the invention wherein the IFNα-free period lasts up to about 2, 3, 4 or up to about 5 days.

In another further embodiment, the invention provides a use or a method according to the invention wherein the IFNα-free (ii) period lasts up to about 2 days, or up to about 4 days.

In another further embodiment, the invention provides a use or a method according to the invention wherein the chemotherapy period lasts up to about 1 or about 2 months.

In another further embodiment, the invention provides a use or a method according to the invention wherein the chemotherapeutic agent is Cytarabine or a derivative thereof.

In another further embodiment, the invention provides a use or a method according to the invention wherein the chemotherapeutic agent is 5-fluorouracil or a derivative thereof.

In another further embodiment, the invention provides a use or a method according to the invention wherein the chemotherapeutic agent is Cisplatin or a derivative thereof.

In another further embodiment, the invention provides a use or a method according to the invention wherein the chemotherapeutic agent is a Taxen or derivative thereof.

In another further embodiment, the invention provides a use or a method according to the invention wherein the chemotherapeutic agent is Imatinib or other BCR-ABL kinase inhibitor or derivative thereof.

In another further embodiment, the invention provides a use or a method according to the invention wherein the chemotherapeutic treatment is a combination of Cytarabine or a derivative thereof and Imatinib or other BCR-ABL kinase inhibitor or a derivative thereof.

In another further embodiment, the invention provides a use or a method according to the invention wherein the chemotherapeutic treatment is a combination of 5-fluorouracil or a derivative thereof and Imatinib or other BCR-ABL kinase inhibitor or a derivative thereof.

In another further embodiment, the invention provides a use or a method according to the invention wherein the chemotherapeutic treatment is a combination of Cisplatin or a derivative thereof and Imatinib or other BCR-ABL kinase inhibitor or a derivative thereof.

In another further embodiment, the invention provides a use or a method according to the invention wherein the chemotherapeutic treatment is a combination of Taxen or a derivative thereof and Imatinib or other BCR-ABL kinase inhibitor or a derivative thereof.

In another further embodiment, the invention provides a use or a method according to the invention wherein the administration pattern comprises at least one or several cycles of the administration pattern according to the invention, i.e. at least one or several cycles of steps (i) to (iii).

In another further embodiment, the invention provides a use or a method according to the invention wherein the administration pattern according to the invention further comprises a step (iv) after step (iii) wherein step (iv) comprises a chemotherapy free period.

In another further embodiment, the invention provides a use or a method according to the invention wherein the administration pattern comprises at least one or several cycles of the administration pattern according to the invention, i.e. at least one or several cycles of steps (i) to (iv).

In another further embodiment, the invention provides a use or a method according to the invention wherein the cancer is selected from leukaemia, lymphoma and melanoma

EXAMPLES

The following abbreviations refer respectively to the definitions below:

h (hour), mg (milligram), pg (microgram), g (gram), wt (wild-type), BrdU (Bromodeoxyuridine), CSC (cancer stem cells), FACS (Flurorescent-activated cell sorting), 5FU (5-Fluoro-uracil), HSC (Hematopoietic stem cells), KO (knock-out), IFN (interferon), U (Unit).

Example 1

Effect of IFN Aloha Treatment on Hematopoietic stem cells (HSCs)

Wild-type C57B1/6 mice were treated with IFNα which was obtained as decribed in the literature (*Le Bon et al.,* 2003, *Nat. Immunol.* 4(10):1009-15). at 0 h and 24 h, respectively with $10 \times 10^3$ U/mouse, and were then treated at 36 h with Bromodeoxyuridine (BrdU) at 360 µg/mouse for cell detection. Mice which were only injected with BrdU were used as control. Bone marrow was then taken from the long bones of hindlegs and prepared by standard procedures (*Wilson et al.,* 2004, *Genes & Dev* 18; 2747-2763). Bone marrow cells were then stained with a cocktail of conjugated antibodies (Bioscience) against mice lineage markers (CD4, CD8, CD11b, Gr1, Ter119, B220), CD117 (c-kit), Sca1 (Ly-6A/E), CD34, CD135, CD48 or CD150). Cells were then fixed. BrdU uptake was analyzed using the BrdU staining kit (BD Biosciences).

Five and six-color fluorescent-activated cell sorting (FACS) analysis (FITC, PE, PE-Cy5, PE-Cy7, APC, APC-Cy7) were performed using a FACS Canto flow cytometer (Becton Dickinson) as described in the literature (*Wilson et al.,* 2004, above). Data were analyzed using FlowJo (Tree Star, Inc.; Ashland, USA software).

Percentages of BrdU positive KLS-HSCs cells (lineage CD117+Sca1+) were determined as a measurement of the proliferation rate of these cells. The same BrdU analyses were performed on subpopulations of HSCs.

Figure 1A:
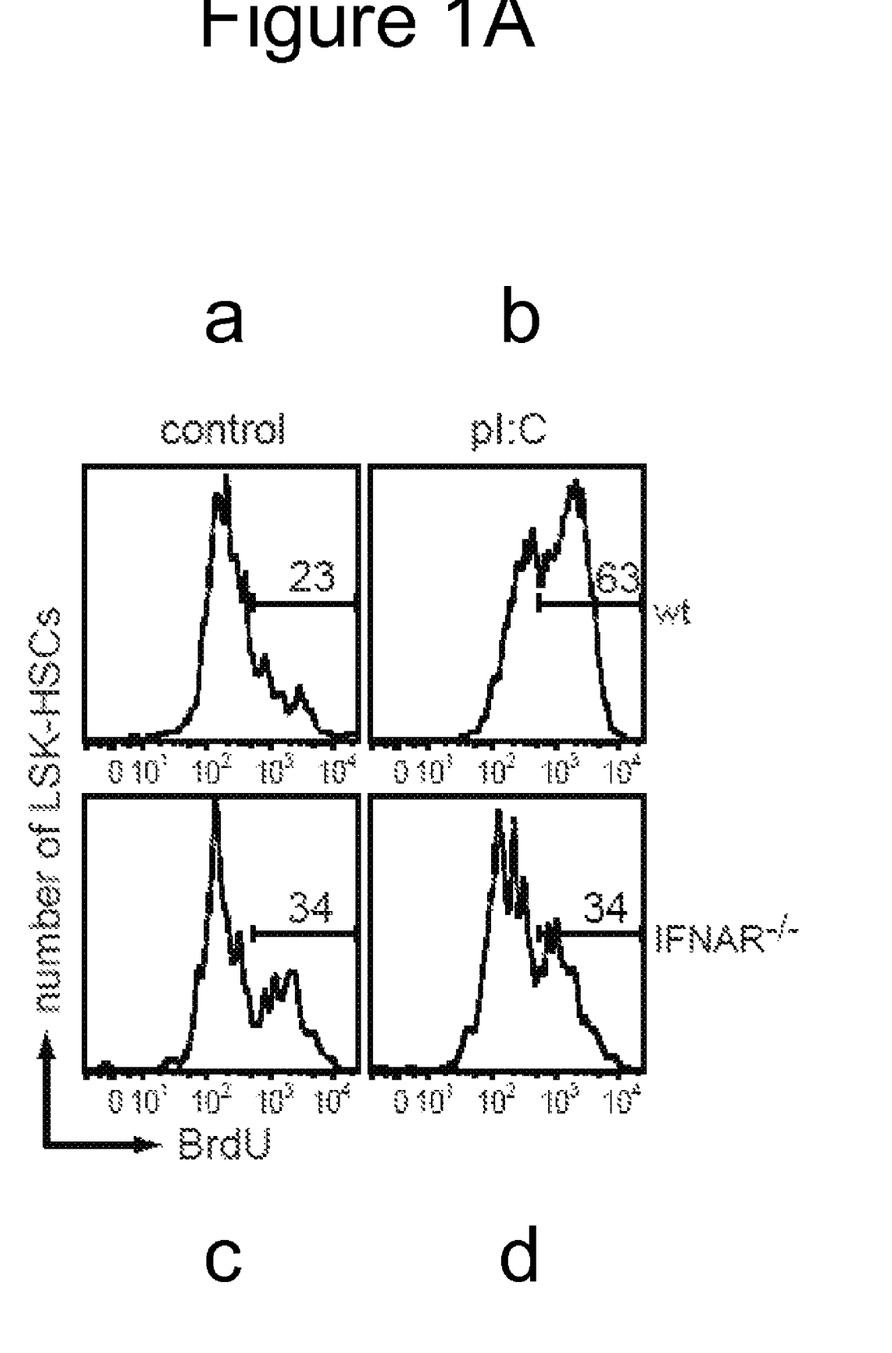
FIG. 1A shows the effect of IFNα treatment on hematopoietic stem cells (HSCs) of C57B1/6 mice (KLS, e.g. lineage-CD117+Sca1+) by representing the kinetics of BrdU uptake of these cells in C57B1/6 wild-type (Wt) untreated mice used as control (FIG. 1A (a)), in C57B1/6 Wt mice treated once at 10,000 U/g with IFNα (FIG. 1A(b)), in IFN receptor knock-out (IFNAR−/−) untreated mice used as a control (FIG. 1A(c)), and in IFN receptor knock-out mice (IFNAR−/−) treated once at 10 µg/g with polyIC (FIG. 1A(d)) as described in Example 1.
Figure 1B:
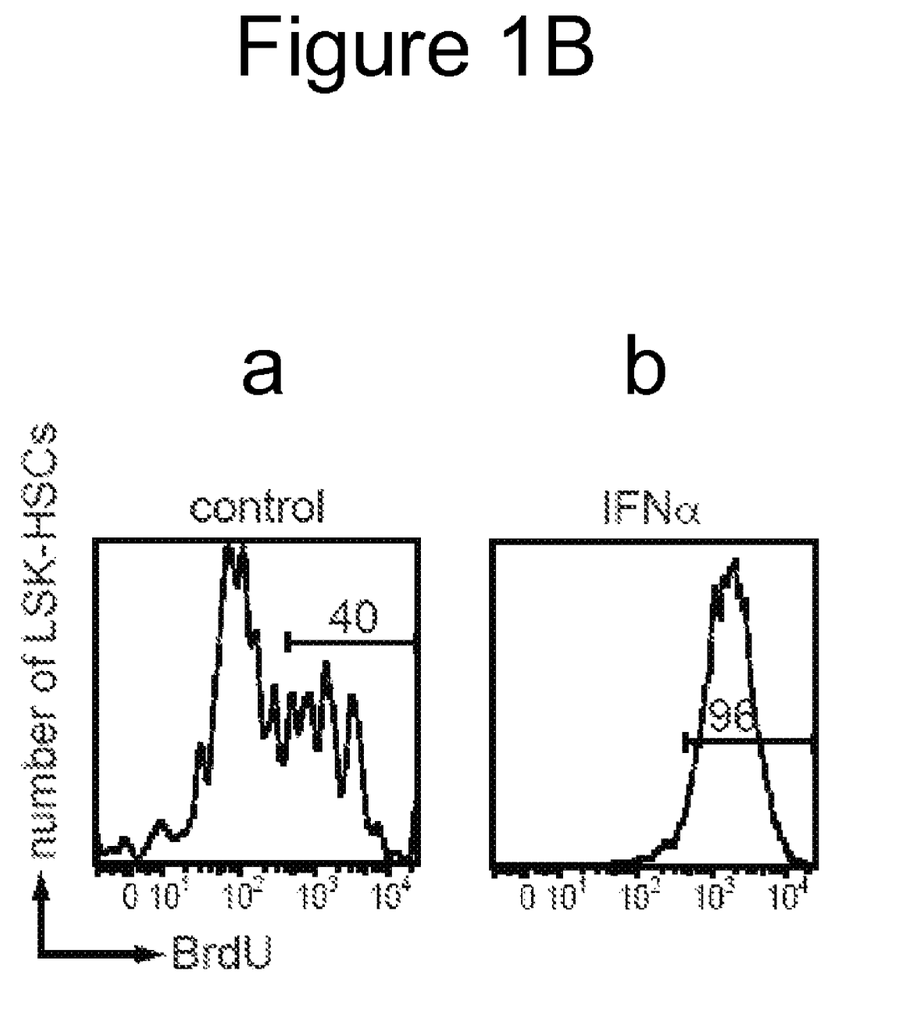
FIG. 1B represent the kinetics of BrdU uptake of HSC subpopulations in C57B1/6 wild-type (Wt) untreated mice used as control (FIG. 1B(a)) and in C57B1/6 Wt mice treated once at 10,000 U/g with IFNα (FIG. 1B(b)) as described in Example 1.
Figure 1C:
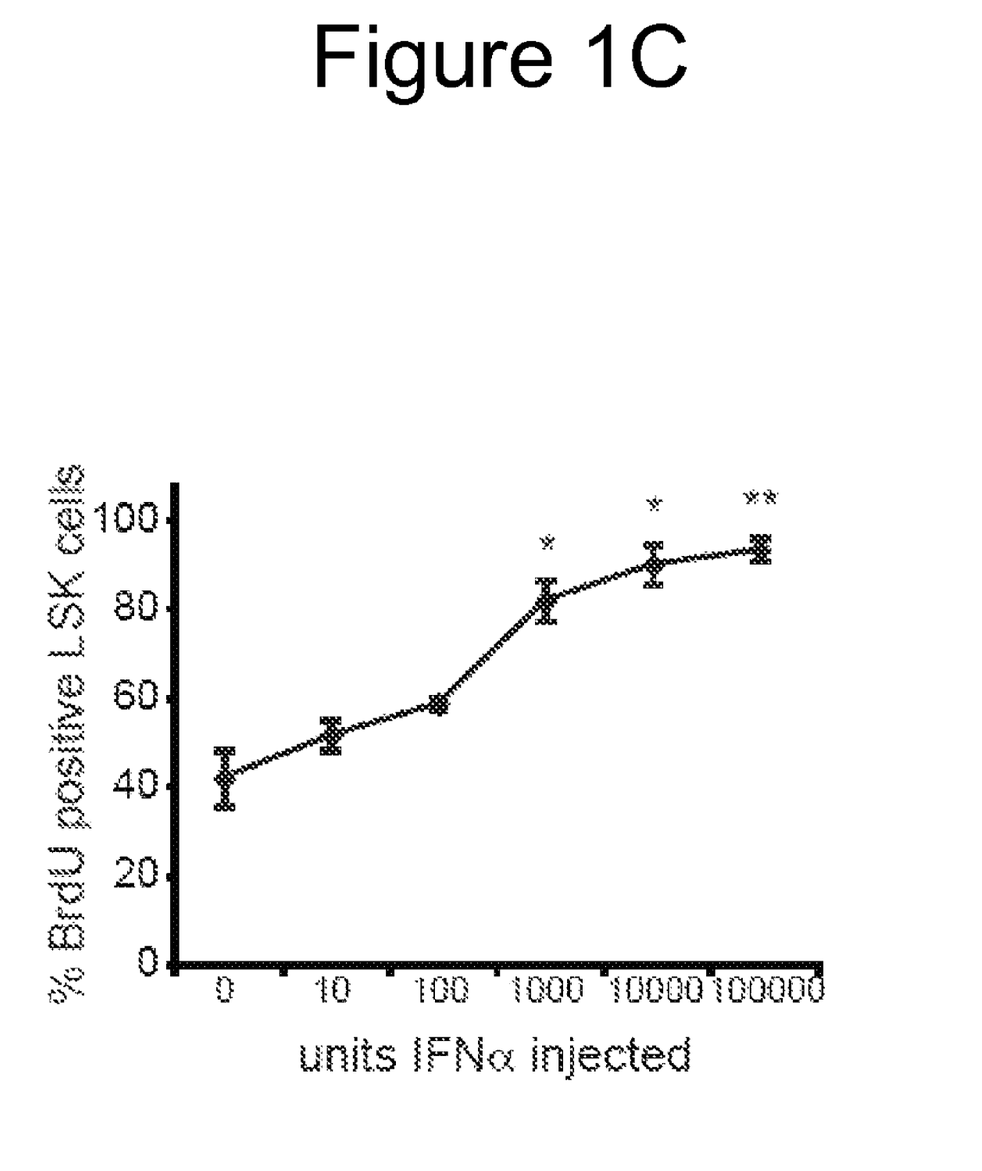
FIG. 1C represents the percentage of BrdU stained KLS cells (BrdU) for different doses of IFNα (in unit IFNα/g of mouse) in mice in comparison of untreated C57B1/6 Wt mice (0).

As shown in FIG. 1A, IFNα treatment increases the proliferation rate of HSCs (in this case lineage-CD117+Sca1+ cells) from 23 to 63% (FIG. 1A(a) and FIG. 1A(b) respectively). This effect is not seen after injection of polyIpolyC, a double stranded RNA mimetic strongly inducing IFNα/b, in IFNAR–/– mice (FIG. 1A(c+d)), indicating that the effect on the HSCs is via IFN signaling. Detailed analysis revealed an increase in proliferation in all subpopulations of HSCs (CD150+, CD34–, CD 150+, CD48– and CD135–, CD34–, also called long-term-HSCs; CD135–, CD34+, also called short-term-HSCs and CD135–, CD34–, also called multipotent progenitors (MPPs)) after IFNα treatment (FIG. 1B).Treatment of IFNα also led to an increase in absolute cell numbers of HSCs. The increase in proliferation after IFNα treatment is dose-dependent (FIG. 1C).

Example 2

Effect of IFN Aloha Treatment on Dormant Hematopoietic Stem Cells (HSCs)

Figure 1D:
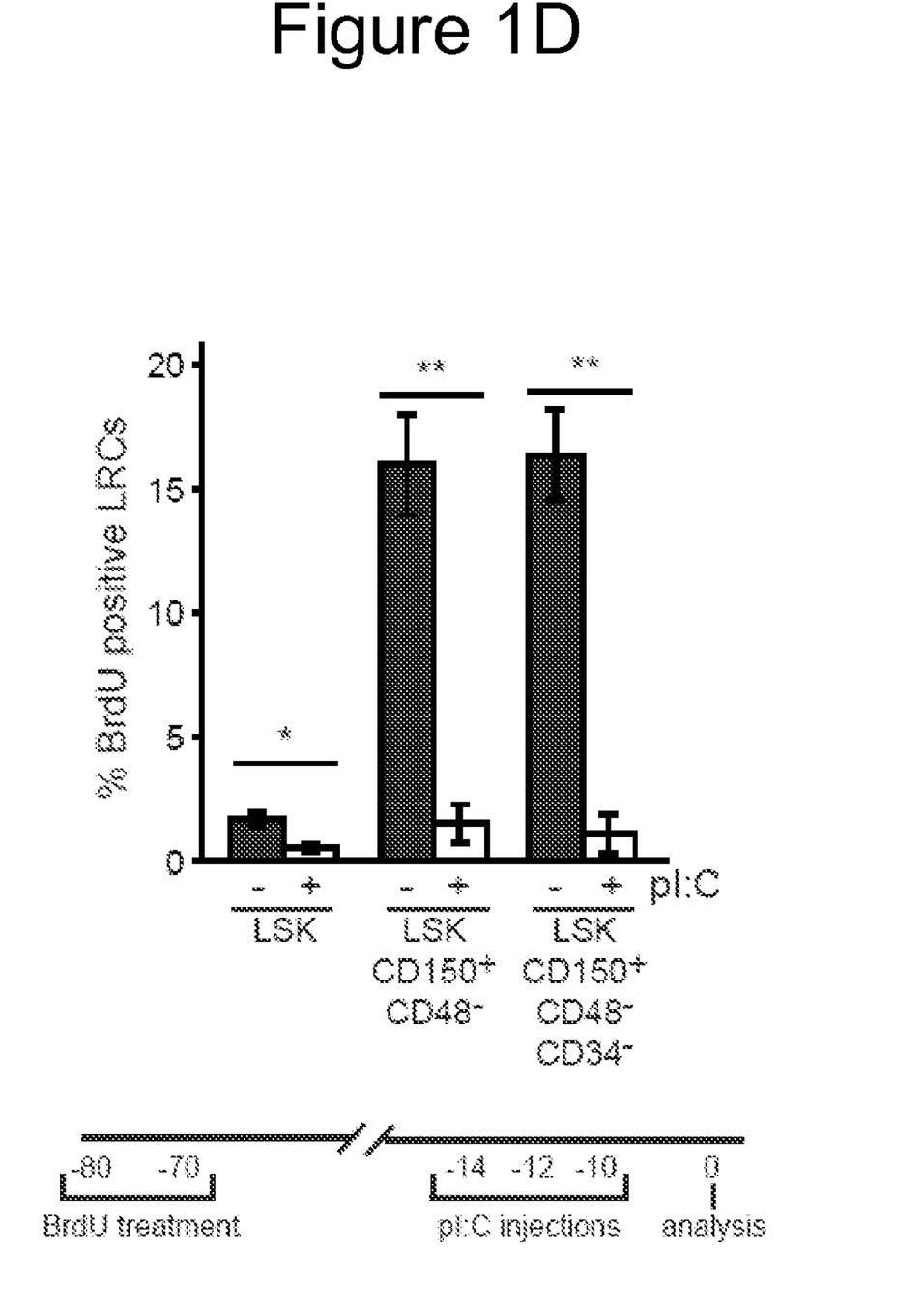

C57B1/6 mice and IFNAR–/– mice were given BrdU (0.8 mg/ml; Sigma) in the drinking water for 10 days. After this BrdU pulse, mice were left for a chase of 10 weeks. Then, mice were twice injected with IFNα at a concentration of $10 \times 10^3$ U/mouse each (48 h gap between the 2 injections) or left untreated. BrdU uptake was then analyzed 10 days after the last IFNα injection. After this BrdU pulse-chase experiment in wild-type mice, about 15% of the long-term HSCs (KLS CD150+CD48–CD34–) are still labeled with BrdU (label retaining cells-LRCs). However, IFNα treatment dramatically reduced the number of LRC+ long-term HSCs, indicating that most of these cells entered the cell cycle by which the BrdU label is diluted out. Importantly, these data show that IFNα activates the dormant HSCs by promoting them to enter the cell division cycle. This was not the case with long-term HSCs lacking the IFN-receptor (in IFNAR–/– mice) showing that this effect is indeed mediated by Interferon signaling (FIG. 1D).

Example 3

Direct Effect of IFN Aloha Treatment on Activation of Hematopoietic Stem Cells (HSCs)

Figure 2A:
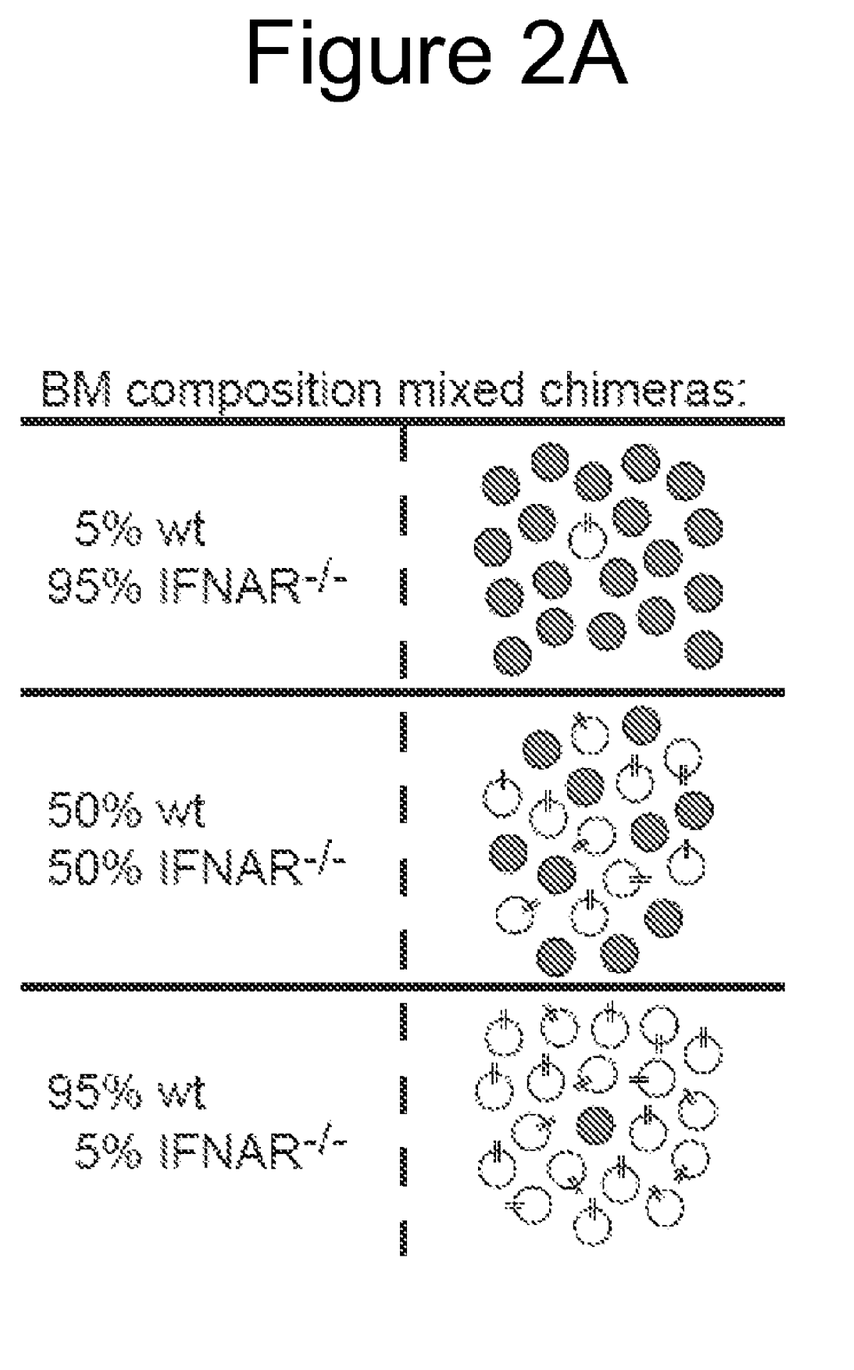
FIG. 2A shows the different mixtures of bone marrow cells comprising various ratios of wild-type (wt) and IFNAR−/− (IFNRKO) bone marrow cells. The different mice were treated with IFNα (10×103 U/mouse) in comparison with untreated wt mice (C) as described in Example 3.
Figure 2B:
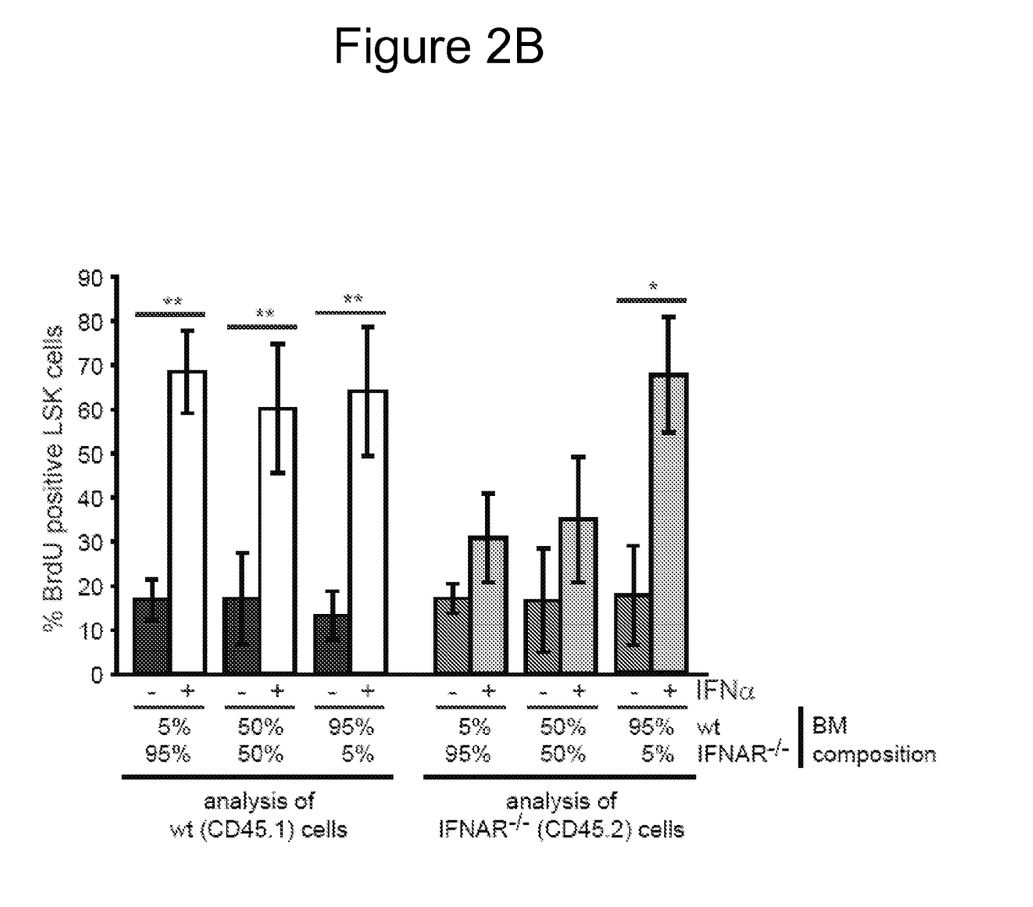
FIG. 2B represents the BrdU uptake in wt (CD45.1) and IFNAR−/− (CD45.2) LSK cells in the mixed bone marrow chimeras in response to treatment with IFNα.

To investigate whether HSCs respond directly to IFNα in vivo, mixed bone marrow "chimeras" comprising various ratios of wild-type (wt) and IFNAR–/– (IFNRKO) bone marrow cells were treated with IFNα ($10 \times 10^3$ U/mouse) in comparison with untreated wt mice (C) (FIG. 2A). The experiment revealed a direct and an indirect activation of HSCs by IFNα (FIG. 2B).

Altogether, these date show that treatment of mice with IFNα induces efficient cell cycle entry of quiescent hematopoietic stem cells (HSCs) (KLS CD150+ CD34– CD48–), indicating that dormant HSCs are activated to proliferate and self-renew. Pulsed IFNα treatment also increases the total number of HSCs. Data obtained by bone marrow chimeras which contained a mix of normal cells and ones deficient for the IFN-receptor suggest that the observed activation is caused at least in part by a direct effect of IFNα on HSCs. To our knowledge this is the first report showing that IFNα has a specific effect on HSCs. Strikingly, this activation effect on HSCs is directly opposite to its growth inhibitory effect described in all other cell types.

Example 4

Sequential Treatment Protocol with IFN Alpha "Pulse" and a Chemotherapeutic Agent (5-Fluoro-uracil)

Wild-type C57B1/6 and IFNAR–/– mice were treated as follows: mice were injected with $10_{25}$ µg/g mouse polyIC (Invivogen) twice (polyIC is a double stranded RNA mimetic strongly inducing IFNα/b), the lag time between the two injections being 48 h. PolyIC injections are used in this experiment as IFN alpha "pulse". Mice that were only treated with 5FU without priming injections of polyIC were used as controls.

5-Fluoro-uracil (5FU) was injected (150 mg/kg, Sigma) at different times after the last polyIC injection: 0 h (same time as last polyIC injection); 24 h, 48 h, 72 h, 5 days and 7 days. The proliferation rate of cells at time of 5FU injection was analyzed by BrdU analysis of KLS cells as described in the above examples. Single 5FU injections were repeated every 7 days. The survival of the mice was monitored for a period of 20 days.

Figure 3A:
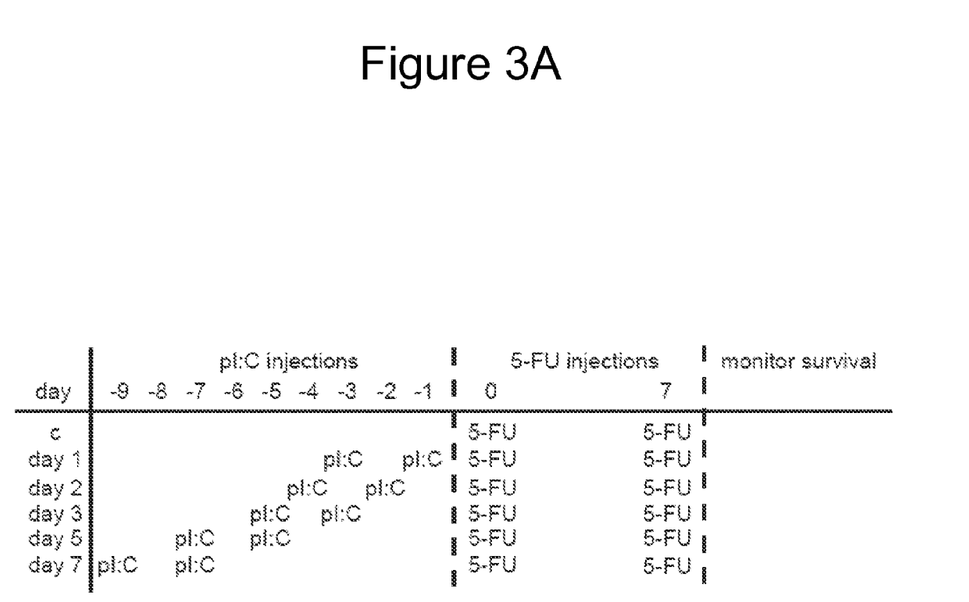
FIG. 3A represents the treatment schedule for polyIC (pI:C) and 5-FU injections.
Figure 3B:
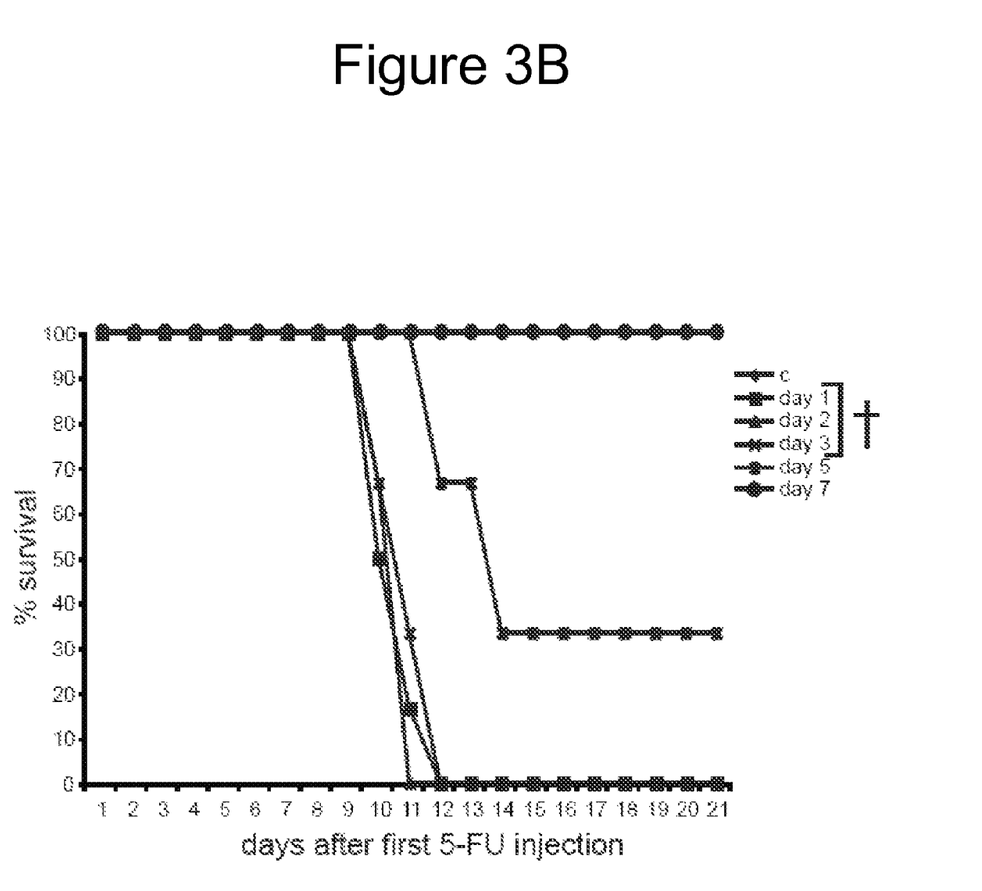
FIG. 3B represents the survival curve of mice up to 20 days after the first 5-FU treatment and FIG. 3C represents the percentage of proliferating, BrdUpositive HSCs at the time of the first 5-FU injection.
Figure 3C:
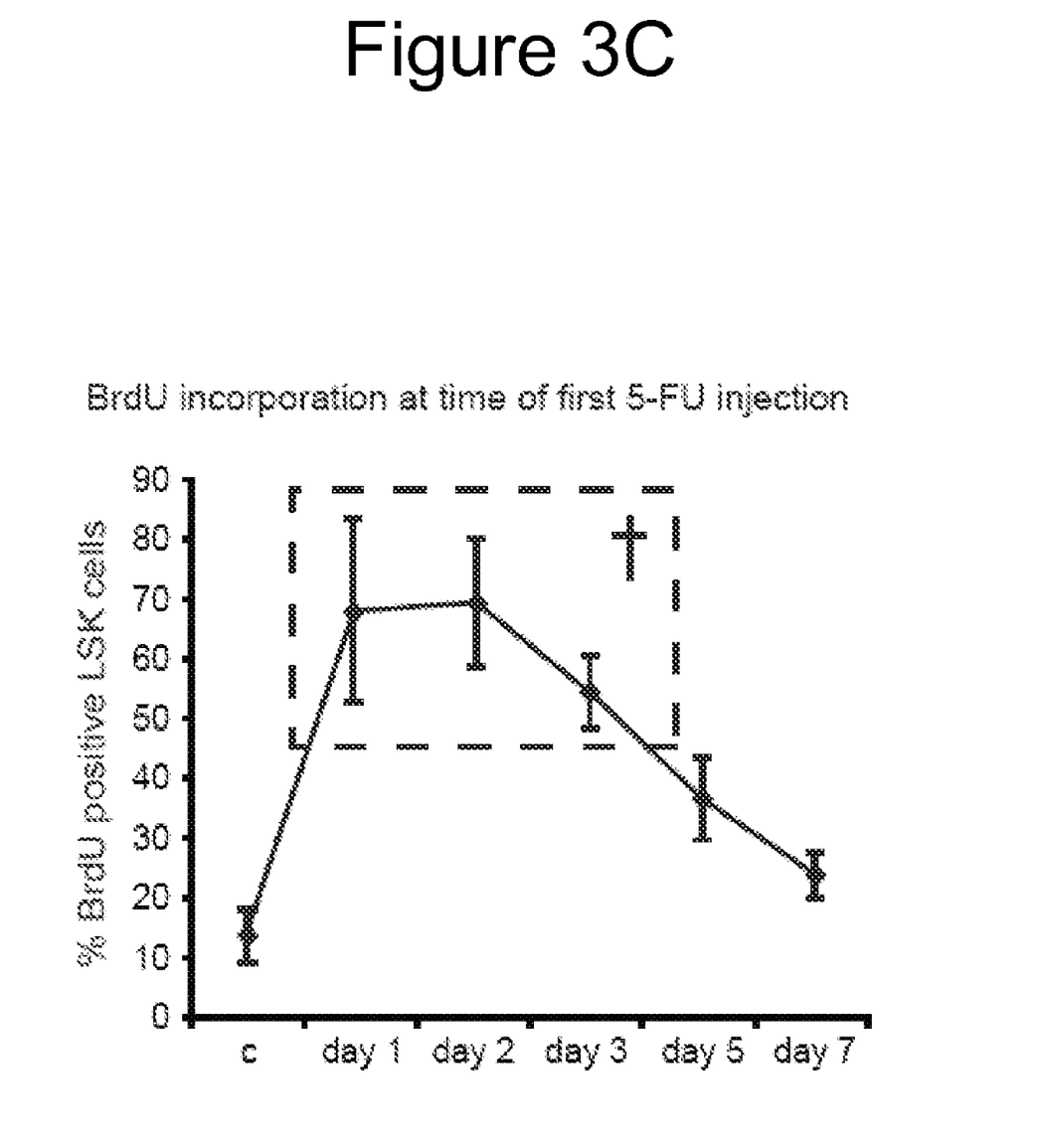

As shown in FIG. 3, untreated mice do survive the repeated treatment with the chemotherapeutic agent 5FU, which causes a massive myeloid ablation due to elimination of all proliferating cells. The mice survive since the dormant HSCs are resistant to 5FU and can generate new progenitors and mature blood cells which quickly restore a functional hematopoietic system. In contrast, injection of polyIC (which induces IFNα) prior to 5FU causes efficient lethality of the mice caused by the efficient elimination of all HSCs. This was most efficient if polyIC was injected 24 to 72 hrs prior to the 5FU treatment. The efficiency of the death of the mice correlates well with the percentage of proliferating HSCs (89%-93%). The same experiment repeated with IFNAR−/− mice revealed no effect on the survival of the mice, showing that the effect of polyIC is mediated by type I IFN signaling. These data show that IFN signaling promotes the efficient entry of normally mostly dormant HSCs into the cell cycle making them susceptible to killing by the anti-proliferative drug 5FU. T represents the time of injection of 5FU after the last polyIC injection; represents the proportion of dead mice at the end of the 20 days and % BrdU+ represents the percentage of proliferating, BrdU positive HSCs.

Example 5

Sequential Treatment Protocol with IFN Alpha Injection and a Chemotherapeutic Agent (Cytarabine)

Mice are transplanted with human leukemic cells derived from patients with acute myeloid leukemia (AML). Mice showing first signs of leukemia are injected with two pulses of human IFN alpha followed by a 2-week-treatment with Cytarabine by injection beginning at 2 days after the last IFN alpha treatment. If necessary, this regimen is repeated every 4 weeks. Tumor expansion and survival of mice is monitored and bone marrow is transplanted into secondary mice recipients to show that leukemic cancer stem cells have been eliminated by this novel sequential treatment strategy.

The results of these sequential treatment protocols combining IFN alpha with the sequential treatment of a chemotherapeutic agent (5-Fluorouracil or Cytarabine) which leads to the elimination of all functional HSCs, shows that combining IFNα treatment with cell cycle blocking chemotherapeutic agents would eliminate cancer stem cells and therefore would prevent tumour relapses and lead to long-term cure from cancer, likely including metastatic malignancies.

What is claimed is:

1. A method for the treatment of a cancer selected from the group consisting of leukemia, lymphoma and melanoma, said method comprising the administration of interferon (IFN) alpha or a pharmaceutical formulation comprising said IFN alpha to a patient in need thereof, said method comprising the following steps:
(i) an induction period wherein a therapeutically effective amount of IFN alpha is administered, said induction period having a maximum duration of about 4 days; then
(ii) an IFN alpha-free period wherein no IFN alpha is administered; and then
(iii) a chemotherapy period wherein a therapeutically effective amount of a chemotherapeutic agent is administered.

2. The method according to claim 1, wherein the induction period has a maximum duration selected from the group consisting of about 2 days and about 3 days.

3. The method according to claim 1, wherein the IFN alpha-free period has a maximum duration selected from the group consisting of about 2 days, about 3 days, about 4 days and about 5 days.

4. The method according to claim 1, wherein the IFN alpha-free period has a maximum duration selected from the group consisting of about 2 days and about 4 days.

5. The method according to claim 1, wherein the chemotherapy period has a maximum duration selected from the group consisting of about 1 month and about 2 months.

6. The method according to claim 1, wherein the chemotherapeutic agent is cytarabine or a derivative thereof.

7. The method according to claim 1, wherein the chemotherapeutic agent is 5-fluorouracil or a derivative thereof.

8. The method according to claim 1, wherein the chemotherapeutic agent is cisplatin or a derivative thereof.

9. The method according to claim 1, wherein the chemotherapeutic agent is a taxen or a derivative thereof.

10. The method according to claim 1, wherein the chemotherapeutic agent is one selected from the group consisting of imatinib, another BCR-ABL kinase inhibitor and derivatives thereof.

11. The method according to claim 1, wherein the chemotherapeutic agent is a combination of cytarabine or a derivative thereof and one selected from the group consisting of imatinib, another BCR-ABL kinase inhibitor and derivatives thereof.

12. The method according to claim 1, wherein the chemotherapeutic agent is a combination of 5-fluorouracil or a derivative thereof and one selected from the group consisting of imatinib, another BCR-ABL kinase inhibitor and derivatives thereof.

13. The method according to claim 1, wherein the chemotherapeutic agent is a combination of cisplatin or a derivative thereof and one selected from the group consisting of imatinib, another BCR-ABL kinase inhibitor and derivatives thereof.

14. The method according to claim 1, wherein the chemotherapeutic agent is a combination of a taxen or a derivative thereof and one selected from the group consisting of imatinib, another BCR-ABL kinase inhibitor and derivatives thereof.

15. The method according to claim 1, wherein the method further comprises a step (iv) following step (iii), wherein step (iv) comprises a chemotherapy-free period.

16. The method according to claim 1, wherein the method comprises a plurality of cycles of steps (i) to (iii).

17. The method according to claim 15, wherein the method comprises a plurality of cycles of steps (i) to (iv).

* * * * *